US012755477B1

(12) United States Patent
Pollak et al.

(10) Patent No.: US 12,755,477 B1
(45) Date of Patent: Oct. 6, 2026

(54) RECONSTRUCTION OF THREE-DIMENSIONAL IMAGES WITH MULTI-DIMENSIONAL TRANSFER FUNCTIONS FOR VISUALIZATION

(71) Applicant: Chroma Medical Technologies LLC, Fall River, MA (US)

(72) Inventors: Clifford J. Pollak, New York, NY (US); Alex Bruce Myers, Swansea, MA (US)

(73) Assignee: Alex Bruce Myers, Swansea, MA (US)

( * ) Notice: Subject to any disclaimer, the term of this patent is extended or adjusted under 35 U.S.C. 154(b) by 92 days.

(21) Appl. No.: 18/660,971

(22) Filed: May 10, 2024

Related U.S. Application Data

(60) Provisional application No. 63/465,633, filed on May 11, 2023.

(51) Int. Cl.
*G06T 15/08* (2011.01)
*G06T 7/13* (2017.01)
*G16H 30/20* (2018.01)

(52) U.S. Cl.
CPC ................ *G06T 15/08* (2013.01); *G06T 7/13* (2017.01); *G16H 30/20* (2018.01); *G06T 2210/41* (2013.01)

(58) Field of Classification Search
CPC ....... G06F 3/0346; G06F 3/011; G16H 30/20; G06T 17/20; G06T 7/0012; G06T 2210/41; G06T 2207/10132; G06T 2207/30048; G06T 19/00; G06T 7/10
USPC .......................................................... 345/418
See application file for complete search history.

(56) References Cited

U.S. PATENT DOCUMENTS

2021/0369394 A1* 12/2021 Braido .................. G16H 20/40
2022/0066456 A1* 3/2022 Ebrahimi Afrouzi ........................ G06F 3/04883
2022/0270762 A1* 8/2022 Crawford ............... G06V 10/25
2023/0027978 A1* 1/2023 Gaborit .................. G16H 50/20
2023/0230321 A1* 7/2023 Schreckenberg ..... G06F 3/0346 345/419
2024/0310851 A1* 9/2024 Ebrahimi Afrouzi ... G01S 17/87
2024/0331269 A1* 10/2024 Sudarsky ................ G06T 15/08
2024/0339198 A1* 10/2024 Qiu ......................... G06T 15/06
2024/0428926 A1* 12/2024 Schreckenberg ....... G06F 3/012
2025/0095864 A1* 3/2025 Hanratty .................. G06N 3/02

OTHER PUBLICATIONS

Ti CW, Swee SK, Abas FS. Contrast measurement for MRI images using histogram of second-order derivatives. In2017 International Conference on Robotics, Automation and Sciences (ICORAS) Nov. 27, 2017 (pp. 1-5). IEEE.*

(Continued)

*Primary Examiner* — Phu K Nguyen
(74) *Attorney, Agent, or Firm* — XR Medical Imaging

(57) ABSTRACT

The present disclosure relates to systems and methods for reconstructing three-dimensional images with multi-dimensional transfer functions for visualization. In at least one embodiment, a method comprises computing one or more 3D surfaces corresponding to a boundary of a 3D object based at least in part on applying a multi-dimensional transfer function to scalar volume data obtained by a scan of the object; and transmitting data descriptive of the one or more 3D surfaces to an extended reality device to display the 3D representation of the object.

19 Claims, 7 Drawing Sheets

(56) References Cited

OTHER PUBLICATIONS

Lorenz C, Carlsen IC, Buzug TM, Fassnacht C, Multi-scale line segmentation with automatic estimation of width, contrast and tangential direction in 2D and 3D medical images. InInternational Conference on Computer Vision, Virtual Reality, and Robotics in Medicine Mar. 19, 1997 (pp. 233-242). Berlin, Heidelberg.*

Sato Y, Nakajima S, Atsumi H, Koller T, Gerig G, Yoshida S, Kikinis R. 3D multi-scale line filter for segmentation and visualization of curvilinear structures in medical images. InInternational Conference on Computer Vision, Virtual Reality, and Robotics in Medicine Mar. 19, 1997 (pp. 213-222). Berlin, Heidelberg.*

Vidyasaraswathi HN, Hanumantharaju MC. Review of various histogram based medical image enhancement techniques. InProceedings of the 2015 International Conference on Advanced Research in Computer Science Engineering & Technology (ICARCSET 2015) Mar. 6, 2015 (pp. 1-6).*

* cited by examiner

RECONSTRUCTION OF THREE-DIMENSIONAL IMAGES WITH MULTI-DIMENSIONAL TRANSFER FUNCTIONS FOR VISUALIZATION

CROSS-REFERENCE TO RELATED APPLICATION(S)

This application claims the benefit of priority of U.S. Provisional Patent Application No. 63/465,633, filed May 11, 2023, the disclosure of which is hereby incorporated by reference herein in its entirety.

TECHNICAL FIELD

The present disclosure relates to visualization of medical imaging data and, more specifically, to processing medical imaging data for three-dimensional presentation by extended reality (XR) devices.

BACKGROUND

Medical imaging systems allow for scanning a region of a patient's body to reconstruct it three-dimensionally, which can be used to reveal objects hidden by the skin and internal organs for the purposes of diagnosis and treatment. As a result of extended reality (XR) environments (which include augmented, virtual reality, mixed reality, or any variant of a three-dimensional experience), medical imaging has become more intuitive by allowing for much greater visualization of the imaging data obtained from medical imaging systems. Existing commercial systems process the imaging data, which is generally represented as three-dimensional density data, by applying one-dimensional transfer functions. However, these current approaches are not ideal as they typically fail to provide well-defined boundaries between different regions of the scan.

SUMMARY

The following presents a simplified summary of various aspects of the present disclosure in order to provide a basic understanding of such aspects. This summary is not an extensive overview of the disclosure. It is intended to neither identify key or critical elements of the disclosure, nor delineate any scope of the particular embodiments of the disclosure or any scope of the claims. Its sole purpose is to present some concepts of the disclosure in a simplified form as a prelude to the more detailed description that is presented later.

One aspect of the present disclosure relates to a method of reconstructing and displaying a 3D representation of an object from scalar volume data corresponding to a scan of the object with a medical imaging system, the method comprising: computing one or more 3D surfaces corresponding to a boundary of the 3D object; applying a multi-dimensional transfer function to the one or more 3D surfaces; and transmitting data descriptive of the one or more 3D surfaces to an XR device to display the 3D representation of the object.

In at least one embodiment, applying the multi-dimensional transfer function comprises computing a first derivative and a second derivative of the scalar volume data along corresponding 3D spatial axes.

In at least one embodiment, applying the multi-dimensional transfer function comprises computing a first derivative of the scalar volume data along corresponding 3D spatial axes.

In at least one embodiment, the method further comprises: computing a 2D histogram data object comprising axes corresponding to scalar volume data representative of the scanned object and the first derivative, and histogram bins representing a combination of the scalar volume data and the first derivative, wherein the 3D surface is computed based at least in part on the 2D histogram data.

In at least one embodiment, the method further comprises: computing a 2D histogram data object comprising axes corresponding to the scalar volume data, the first derivative, and the second derivative, and histogram bins representing a combination of the scalar volume data, the first derivative, and the second derivative, wherein the 3D surface is computed based at least in part on the 2D histogram data.

In at least one embodiment, the method further comprises: computing a 3D histogram volume data object comprising axes corresponding to the scalar volume data, the first derivative, and the second derivative, and histogram bins representing a combination of the scalar volume data, the first derivative, and the second derivative, wherein the 3D surface is computed based at least in part on the 3D histogram volume data.

In at least one embodiment, the histogram is presented for display by the XR device as one or more adjustable 3D polygons for adjusting the volume data, first derivative, and the second derivative along an axis or axes.

In at least one embodiment, the one or more adjustable 3D polygons comprises an adjustable 3D rectangular prism that allows for slicing inside or outside the displayed 3D volume, wherein the 3D volume is displayed within the 3D rectangular prism or the data is excluded from the 3D rectangular prism.

In at least one embodiment, a configurable endo-panel is presented for display by the XR device, the endo-panel comprising an available tool set follows a user while walking inside the 3D volume.

In at least one embodiment, the method further comprises: prior to computing the one or more 3D surfaces, downsampling the scalar volume data.

In at least one embodiment, computing the one or more 3D surfaces comprises applying an algorithm or method selected from marching cubes volume, direct volume rendering, volume ray casting, raymarching, ray tracing, shear warp, volume segmentation, early ray termination, empty space skipping, texture-based volume rendering, resampling, texture slicing, supersampling, parallel volume rendering, splatting, alpha blending, octree and BSP (binary space partitioning) space subdivision, multiple and adaptive resolution representation, isosurface rendering, maximum intensity projection, translucent, X-ray, domain volume rendering, full volume rendering, volumetric function interpolation, digital differential analyzer, non-photorealistic volume rendering, pre-integrated volume rendering, multi-pass occlusion culling, volumetric global illumination, spectral volume rendering, temporal reuse of voxels, high definition volume rendering, image-based meshing, Insight Toolkit (ITK) volume generation, noise, interpolation, linear filtering, cardinal spline function, central differencing, object-order, image-order, hybrid, anti-aliasing, aliasing, blurring, gradient filtering, pre-classified rendering, post-classified rendering, Taylor series expansion, front-to-back compositing, back-to-front compositing, gaussian filtering, post-classified model, Riemann sum, proximity clouds, image-level intermixing, accumulation level intermixing, illumination model level intermixing, time-critical rendering, issue, low-albedo optical model, dividing cubes, trimmed voxel lists, a marching tetrahedrons algorithm, or a combination thereof.

In at least one embodiment, transmitting the data descriptive of the one or more 3D surfaces comprises serializing the data into byte arrays.

In at least one embodiment, the data descriptive of the one or more 3D surfaces is transmitted to the XR device as a 3D texture data object.

In at least one embodiment, the XR device is configured to display multiplanar reconstructions of the one or more 3D surfaces.

In at least one embodiment, scalar volume data is derived, extracted, or otherwise obtained from data stored in a data object generated by the medical imaging system during the scan of the object, wherein the data object is a Digital Imaging and Communications in Medicine (DICOM) format, a Neuroimaging Informatics Technology Initiative format, or a Nearly Raw Raster Data (NRRD) format.

In at least one embodiment, the scalar volume data corresponds to data obtained from one or multiple modalities selected from an arthogram scan, a computer tomography scan, an echocardiograph scan, an elastograph scan, a near-infrared spectroscopy scan, a magnetic particle imaging scan, a magnetic resonance imaging scan, a mammography scan, a myelogram scan, a photoacoustic imaging scan, a digital histopathology scan, a positron emission tomography scan, a projectional radiography scan, a tomosynthesis scan, an ultrasound scan, an x-ray scan, or any other medical scanner that produces DICOM images.

In at least one embodiment, the XR device comprises an augmented reality (AR) device or a virtual reality (VR) device.

In at least one embodiment, the method further comprises transmitting data descriptive of the one or more 3D surfaces to a plurality of XR devices simultaneously or near-simultaneously.

In at least one embodiment, the plurality of XR devices are configured to view the 3D representation of the object within the same XR environment.

In at least one embodiment, the method further comprises: applying one or more machine learning algorithms to the one or more 3D surfaces for image classification and object detection.

A further aspect of the present disclosure relates to a method of presenting for display a 3D representation of an object by an XR device, the method comprising: receiving, by the XR device: data descriptive of one or more 3D surfaces representative of the object, the data derived from multi-dimensional transfer function applied to scalar volume and multivariate data corresponding to a scan of the object; 3D histogram volume data descriptive of axes corresponding to scalar volume data representative of the scanned object; and generating for display the one or more 3D surfaces representative of the object based on the 3D histogram volume data.

In at least one embodiment, the method further comprises: presenting for display a 3D histogram volume data object comprising axes corresponding to the scalar volume data, the first derivative, and the second derivative, and histogram bins representing a combination of the scalar volume data, the first derivative, and the second derivative, wherein the 3D surface is computed based at least in part on the 3D histogram volume data.

In at least one embodiment, the histogram is presented for display by the XR device as one or more adjustable 3D polygons for adjusting the volume data, first derivative, and the second derivative along an axis or axes.

In at least one embodiment, the one or more adjustable 3D polygons comprises an adjustable 3D rectangular prism that allows for slicing inside or outside the displayed 3D volume, wherein the 3D volume is displayed within the 3D rectangular prism or the data is excluded from the 3D rectangular prism.

In at least one embodiment, a configurable endo-panel is presented for display by the XR device, the endo-panel comprising an available tool set follows a user while walking inside the 3D volume.

A further aspect of the present disclosure relates to a system for providing three-dimensional visualization of an object, the system comprising: a client computing device and/or a server; and an XR device operatively coupled to the client computing device and/or the server, wherein the client computing device and/or the server are adapted to perform any one of the preceding methods.

A further aspect of the present disclosure relates to a non-transitory computer-readable medium having instructions encoded thereon that, when executed by a processing device, cause the processing device to perform any one of the preceding methods.

BRIEF DESCRIPTION OF THE DRAWINGS

In order to facilitate a fuller understanding of the present disclosure, reference is now made to the accompanying drawings, in which like elements are referenced with like numerals. These drawings should not be construed as limiting the present disclosure, but are intended to be exemplary only.

DETAILED DESCRIPTION

Figure 1:
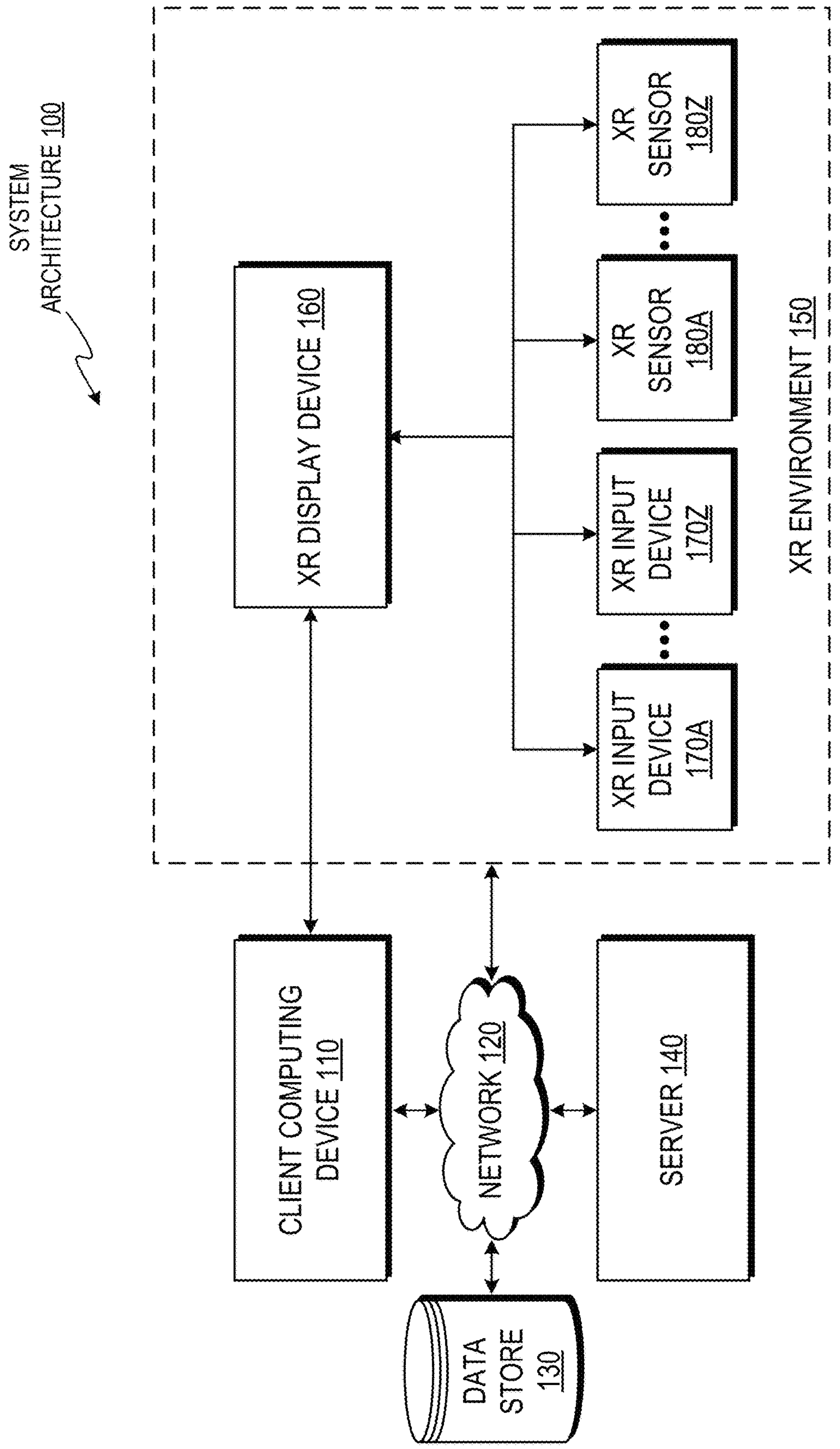
FIG. 1 illustrates an exemplary system architecture, in accordance with at least one embodiment.

Embodiments of the present disclosure relate to systems and methods for reconstructing three-dimensional (3D) images for visualization, for example, in an extended reality (XR) environment. Further, certain embodiments relate to the utilization of multi-dimensional transfer functions based on, for example, first and second derivatives of the data values in the imaging data to produce well-defined boundaries. The methodologies described herein overcome the deficiencies in current approaches that result in erroneously drawn boundaries by utilizing one-dimensional transfer functions. In medical imaging, volume rendering is a computer graphics technique for displaying DICOM ("Digital Imaging and Communications in Medicine") datasets through a three-dimensional volume or two-dimensional image to provide improved visualization of human anatomy applicable for surgical planning and medical education. The DICOM format is a standard format used to store, manage, and transmit medical images and related data, such as patient information and diagnostic reports. DICOM data is typically generated by medical imaging devices such as X-ray machines, computer tomography (CT) machines, magnetic resonance imaging (MRI) machines, ultrasound machines, and other devices. These scanning devices produce images that can be saved in DICOM format. DICOM data may further contain information about the patient, the imaging modality, the date and time of the scan, and various other parameters related to the acquisition and processing of the image.

DICOM data is typically stored in a PACS (Picture Archiving and Communication System) which is a medical image management system that allows for storage, retrieval, and distribution of DICOM images and related information. The use of a standard format like DICOM allows for compatibility between different imaging systems, which helps to ensure that patient data can be easily accessed and shared across different healthcare organizations. The size of DICOM data sets can vary widely depending on a number of factors, including the type of medical imaging modality used, the size and resolution of the images, and the number of images acquired during a given scan. For example, a single DICOM file from a digital X-ray image may be just a few hundred kilobytes in size, while a DICOM file from a high-resolution CT scan or MRI may be several hundred megabytes or even several gigabytes in size. In addition to the size of individual DICOM files, the total size of a DICOM data set can also vary depending on the number of images acquired during a scan, as well as any associated data such as patient information, clinical reports, or annotations. Therefore, due to this variability in size, it is important to carefully manage and store DICOM data to ensure that it can be easily accessed and shared among healthcare providers as needed. This variability can also be difficult to process DICOM data for visualization purposes.

Embodiments of the present disclosure provide methods for image reconstruction AR and VR devices (XR devices) from medical imaging data, such as DICOM data, for which the image quality of the reconstruction image can be manipulated in a way that facilitates boundary disambiguation, analysis, and classification. In certain embodiments, such methods utilize 2D and 3D multidimensional transfer functions to provide additional dimensions to neighboring voxels and samples in density data. Moreover, certain embodiments can process the data sets on a device prior to transmitting to the XR device to account for limited storage space and processing capabilities of the XR device.

In at least one embodiment, use of a 3D transfer function can disambiguate boundaries and entities using the derivative of gradient magnitude, thus producing a more realistic representation of the varying objects within the generated volume. The data value f(x), directional derivative f(x) of the gradient, and second directional derivative along the gradient direction can be used to generate a 3D histogram that is applied to the data to improve visualization of object boundaries.

Existing medical systems are limited in their ability to disambiguate boundaries between skin and muscle or muscle and tissue, as such systems typically use one-dimensional transfer functions. Such erroneously colored boundaries can result in ambiguity and, at worst, patient misdiagnosis. A one-dimensional transfer function is a mathematical function used in computer graphics and image processing to map a single input value to a corresponding output value. It is typically used to adjust the brightness or contrast of an image or to apply color grading or other visual effects. The input values of a one-dimensional transfer function typically correspond to the intensity values of an image, ranging from 0 (black) to 255 (white) in an 8-bit grayscale image, for example. The output values of the transfer function determine how the input values are mapped to new intensity values, allowing for adjustments to be made to the brightness, contrast, and color of the image.

There are various limitations to using one-dimensional transfer functions for boundary analysis in 3D density data, which include: (1) limited information: one-dimensional transfer functions only allow for a single scalar value to be used for assigning color and opacity to voxels, thus obscuring variations in density along different directions or gradients; (2) ambiguity: one-dimensional transfer functions can lead to ambiguity in boundary detection, particularly if the density distribution is complex or contains multiple regions with similar densities, which can lead to the generation of false boundaries or the failure to detect true boundaries; and (3) subjectivity: the choice of transfer function can vary depending on the specific visualization task or desired effect, leading to inconsistencies or variations in boundary detection depending on the user's preferences or biases.

Embodiments of the present disclosure address these limitations by using multi-dimensional transfer functions. A multi-dimensional transfer function is a type of transfer function used in volume rendering to assign color and opacity to voxels based on scalar and multivariate data values, rather than just one scalar value as in a one-dimensional transfer function. In a multi-dimensional transfer function, each multivariate data value is mapped to a corresponding color and opacity value, resulting in a multi-dimensional color and opacity space. This space can be visualized as a 3D color cube, where each axis represents a different scalar or multivariate data value and the color at any point within the cube represents the assigned color and opacity values for that combination of scalar and multivariate data values.

The scalar values of the data, as well as the values of first and second derivatives computed from the multi-dimensional transfer function, can be used to compute 3D histogram data, which corresponds to a series of bins or cells, each representing a range of values in three dimensions (e.g., x, y, and z). The height of each bin represents the frequency of values falling within the range of that bin. In at least one embodiment, the 3D histogram data can be used in volume rendering to provide more detailed information about the distribution of data in the volume.

Advantages of the present embodiments include, but are not limited to: (1) enlarged modeling techniques that allow a user to walk inside a model for inspection, facilitating diagnosis and early cancer detection for patients; (2) disambiguation of close boundaries between materials, such as bone and tissue; (3) improved data processing that allows for large DICOM data sets to be processed and loaded onto XR devices with limited processing capabilities and memory, such as AR display devices; and (4) simple visualization tools that leverage 3D histogram data to filter 3D transfer function results to highlight key features of the datasets.

As used herein, the term "extended reality" or "XR" encompasses virtual reality (VR), augmented reality (AR), mixed reality (MR), or any variant thereof that provides an immersive 3D experience for a user.

Although embodiments of the present disclosure are discussed in terms of visualization of medical imaging data, the embodiments may also be generally applied to the processing sets of 3D density data for any suitable purpose. Further, although DICOM data sets are exemplified in the various examples, it is to be understood that other data formats are compatible with the embodiments described herein including, but not limited to, Neuroimaging Informatics Technology Initiative (NIfTI) format, Nearly Raw Raster Data (NRRD) format, Geometry format under the Neuroimaging Informatics Technology Initiative (GIfTI), Medical Imaging NetCDF (MINC) format, Analyze format, Medical Research Council (MRC) format, Analysis of Functional NeuroImages (AFNI) format, FMRIB Software Library (FSL) format, and JPEG format.

FIG. 1 illustrates an exemplary system architecture 100, in accordance with an embodiment of the present disclosure. The system architecture 100 includes a client computing device 110, a data store 130, a server 140, an XR display device 160, and one or more peripheral devices related to the operation of the XR display device 160 (e.g., XR input devices 170A-170Z, XR sensors 180A-180Z, etc.). The XR display device and its peripheral devices may collectively provide a XR environment 150. One or more of the devices of the system architecture 100 may be implemented using computer system 700, described below with respect to FIG. 7.

The client computing device 110 can be any suitable computing device such as a personal computers (PC), laptop, mobile phone, smart phone, tablet computer, netbook computers, etc. An individual user may be associated with (e.g., own and/or use) the client computing device 110. As used herein, a "user" may be represented as a single individual. In some embodiments, the client computing device 110 may be used by an individual to facilitate, moderates, or otherwise exercise control over an experience in an XR environment 150 for that individual and/or other individuals. In at least one embodiment, the client computing device 110 may be a wearable device.

The client computing device 110 may implement a user interface, which may allow a user of the client computing device 110 to send/receive information to/from other devices including, but not limited to, the data store 130, the server 140, or any devices associated with the XR environment 150. For example, the user interface may be a web browser interface that can access, retrieve, present, and/or navigate content (e.g., web pages such as Hyper Text Markup Language (HTML) pages). As another example, the user interface may enable data visualization with the client computing device 110. In some embodiments, the user interface may be a standalone application (e.g., a mobile "app," etc.), that allows a user of the client computing device 110 to send/receive information to/from other devices including, but not limited to, the data store 130, the server 140, or any devices associated with the XR environment 150.

In some embodiments, the client computing device 110 may utilize one or more local data stores in lieu of or in combination with the data store 130. Each of the local data stores may be internal or external devices, and may include one or more of a short-term memory (e.g., random access memory), a cache, a drive (e.g., a hard drive), a flash drive, a database system, or another type of component or device capable of storing data. The local data stores may also include multiple storage components (e.g., multiple drives or multiple databases) that may also span multiple computing devices (e.g., multiple server computers). In some embodiments, the local data stores may be used for data back-up or archival purposes.

In some embodiments, the client computing device 110 may include a built-in display or be communicatively coupled to a peripheral display device, such as a liquid crystal display (LCD), a light-emitting diode (LED) display, or a cathode ray tube (CRT). For example, the display device may be utilized to simultaneously display a rendering of a display presented by the XR display device 160, allowing both an individual operating the client computing device 110 to observe a representation of the display of the XR display device 160 to another individual in the XR environment 150.

In at least one embodiment, the client computing device 110 is configured to interface directly with the XR display device 160, for example, via a hardwired connection to the XR display device 160. In at least one embodiment, the client computing device 110 may be physical worn (e.g., as part of a backpack or tethered computer) by the user who is wearing the XR display device 160.

In one embodiment, network 120 may include a public network (e.g., the Internet), a private network (e.g., a local area network (LAN), a wide area network (WAN), or a Bluetooth network), a wired network (e.g., Ethernet network), a wireless network (e.g., an 802.11 network or a Wi-Fi network), a cellular network (e.g., a Long Term Evolution (LTE) network), routers, hubs, switches, server computers, and/or a combination thereof. Although the network 120 is depicted as a single network, the network 120 may include one or more networks operating as a stand-alone networks or in cooperation with each other. The network 120 may utilize one or more protocols of one or more devices that are communicatively coupled thereto. The network 120 may translate protocols to/from one or more protocols of the network devices.

In at least one embodiment, the data store 130 can include one or more of a short-term memory (e.g., random access memory), a cache, a drive (e.g., a hard drive), a flash drive, a database system, or another type of component or device capable of storing data. The data store 130 can also include multiple storage components (e.g., multiple drives or multiple databases) that can also span multiple computing devices (e.g., multiple server computers). In at least one embodiment, the data store 130 can be cloud-based. One or more of the devices of system architecture 100 can utilize their own storage and/or the data store 130 to store public and private data, and the data store 130 can be configured to provide secure storage for private data. In at least one embodiment, the data store 130 can be used for data back-up or archival purposes. In at least one embodiment, the data store 130 may be configured to provide HIPAA-compliant data storage for the purposes of storing and maintaining medical imaging data, such as DICOM data sets. In some embodiments, the data store 130 is implemented using a backend Node.js and RESTful API architecture that facilitates rapid and real-time updates of stored data. In conjunction with Node.js and RESTful API, the functionality of the data store 130 may be implemented with a database such as PostgreSQL deployed on a Kubernetes system.

In some embodiments, the server 140 may include one or more computing devices (such as a rackmount server, a router computer, a server computer, a personal computer, a mainframe computer, a laptop computer, a tablet computer, a desktop computer, etc.), data stores (e.g., hard disks, memories, databases), networks, software components, and/or hardware components. The server 140 may be configured to receive and process medical imaging data and prepare the data for visualization by the XR display device 160.

In at least one embodiment, the XR display device 160 is any type of VR or AR headset that can be secured to the user's head and is capable of generating a VR or AR session. Exemplary VR/AR headsets include, but are not limited to, Oculus Rift®, Oculus Go®, Oculus Quest®, Oculus Quest 2® (Meta Quest 2®), HTC Vive®, Sony PlayStationVR®, a smartphone or computing device placed into a holder that can operate as a VR/AR headset (such as Google cardboard and a smartphone), Microsoft HoloLens®, Nreal Air AR Glasses®, Microsoft HoloLens 2®, Magic Leap Lightwear®, Magic Leap 2®, Epson Moverio BT-300FPV Drone Edition®, Google Glass®, Vuzix Blade AR®, Meta Quest 2®, Meta Quest 3®, Meta Quest Pro®, Optinvent Ora-2®, and Garmin Varia Vision®, and other variants of these devices or other devices that provide similar functionality.

In some embodiments, the XR display device 160 may contain a communications device, a data store, and display driver. The XR display device 160 may also include a network interface device that allows for communication with one or more devices of the system architecture 100. In some embodiments, one or more XR input devices 170A-170Z and one or more XR sensors 180A-180Z may be present and communicatively coupled to the XR display device 160. The XR sensors 180A-180Z may include motion tracking sensors and additional sensors, which may be integrated into the XR display device 160 in certain embodiments. In some embodiments, the motion tracking sensors may utilize one or more inertial measurement unit (IMU) devices. In some embodiments, the additional sensors may include one or more cameras, such as infrared, thermal, or night vision cameras, or one or more eye tracking sensors that may track movement of the wearer's eye(s).

Exemplary XR input devices 170A-170Z include, but are not limited to:

(1) Controllers, that generally include handheld devices that can be used to interact with the XR environment 150. Controllers generally have buttons, triggers, and joysticks that allow users to navigate, interact with objects, and perform actions. Controllers can include conventional gaming controllers, such as those used for Xbox®, HTC® Vive®, Meta®, or Oculus® Touch® devices.

(2) Gloves, which are wearable devices that track the movements of the users hands and fingers. Gloves can provide a more natural and immersive way to interact with objects in the XR environment 150.

(3) Wearable motion trackers, which are sensors that can track the user's movements and translate them into virtual movement through the XR environment 150. Motion trackers can be attached to the user's body, such as on their head, chest, or limbs, to provide accurate tracking of their movements.

(4) Eye tracking devices, which are sensors that can track the user's eye movements and use them to control the XR environment 150. Eye tracking devices can be used to aim, select, and interact with objects in the environment, and can also be used for gaze-based interaction and navigation.

(5) Audio input, which includes the use of microphones and speech recognition software to interpret the user's voice commands and control the XR environment 150. Voice recognition can be a useful input method for hands-free interaction and control, and can be especially useful for users with mobility impairments.

(6) Brain-computer interfaces, which are devices that can detect and interpret brain activity and translate it into commands for the XR environment 150. Brain-computer interfaces can provide a highly immersive and intuitive way to control the environment, and can be especially useful for users with disabilities that affect their mobility or dexterity.

Although the devices of the system architecture 100 are depicted in FIG. 1 as single, disparate components, one or more of the depicted devices may be implemented together in a single device or networked in various combinations of multiple different devices that operate together. In some embodiments, some or all of the functionality of the client computing device 110, the data store 130, or the server 140 may be performed by the XR display device 160. For example, the XR display device 160 may implement a software application that performs some or all of the functions of the client computing device 110 or the server 140.

Figure 2:
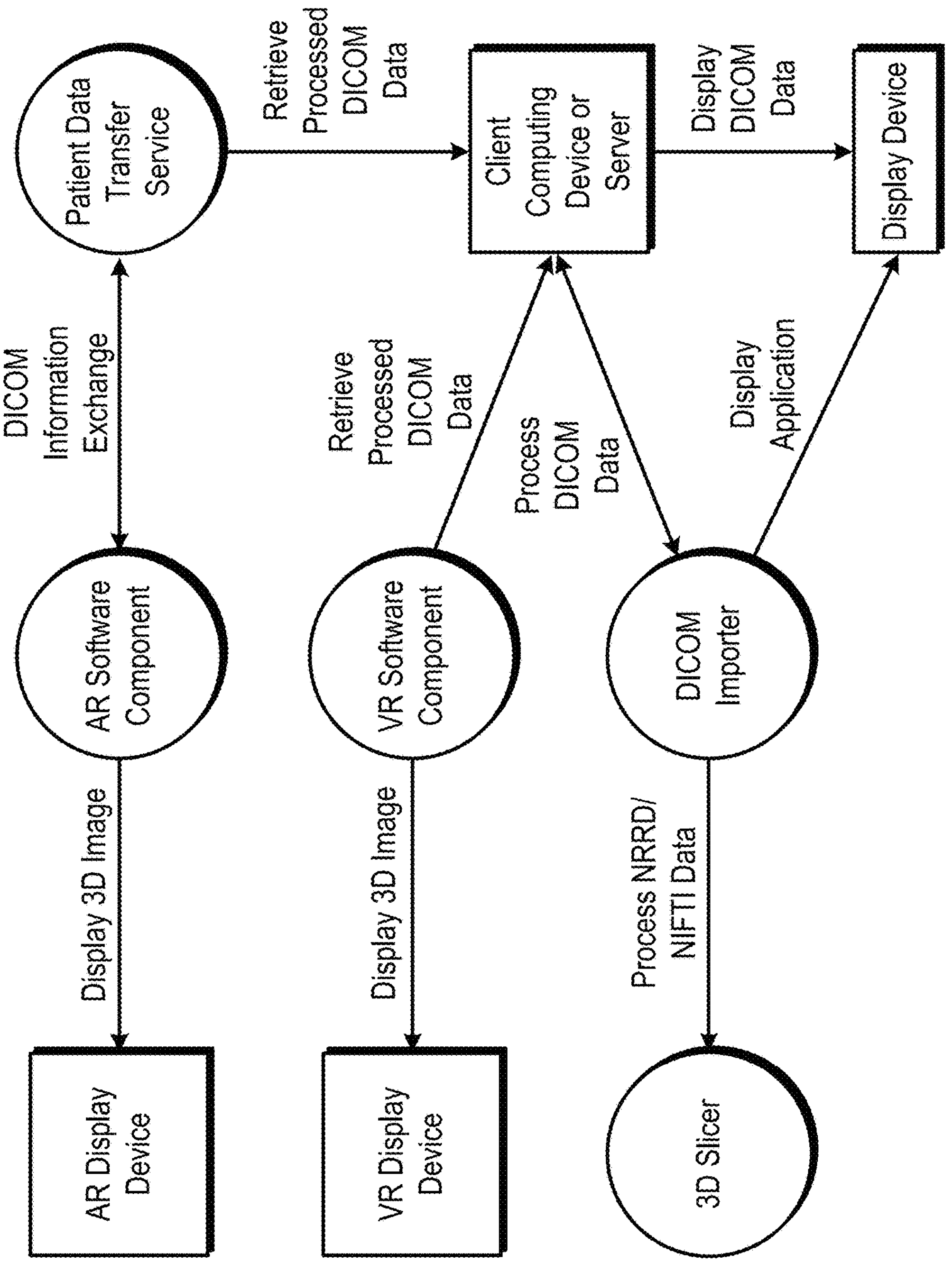
FIG. 2 illustrates a context diagram of the system architecture 100, in accordance with at least one embodiment.

FIG. 2 illustrates a context diagram of the system architecture 100, in accordance with an embodiment of the present disclosure. The rectangles represent physical devices (e.g., representative of one or more of the devices of the system architecture 100), and the circles represent software components (e.g., which may be implemented by one or more of the devices of the system architecture 100), which interface with the physical devices and facilitate operation thereof and data processing.

In at least one embodiment, the DICOM importer component may be implemented by a client computing device or server, which may be operatively coupled to a display device. The DICOM importer component may facilitate display of DICOM data, as well as process NRRD, NITI, or other formats with 3D Slicer or any other medical imaging process system.

In at least one embodiment, the client computing device or server may utilize a patient data transfer service that retrieves DICOM data for one or more patients (e.g., from the data store 130). The AR software component can then process the DICOM data for display by the AR display device. In at least one embodiment, the VR software component processes the DICOM data for display by the VR display device. In at least one embodiment, processed DICOM data is transferred locally via a hard-wired connection or via a wireless connection. The client computing device or server can be operated by, for example, a clinician or clinical assistant to retrieve DICOM, NRRD, or NIfTI data files via the Internet, a local network, or a media device to store locally on the client computing device or server.

Figure 3:
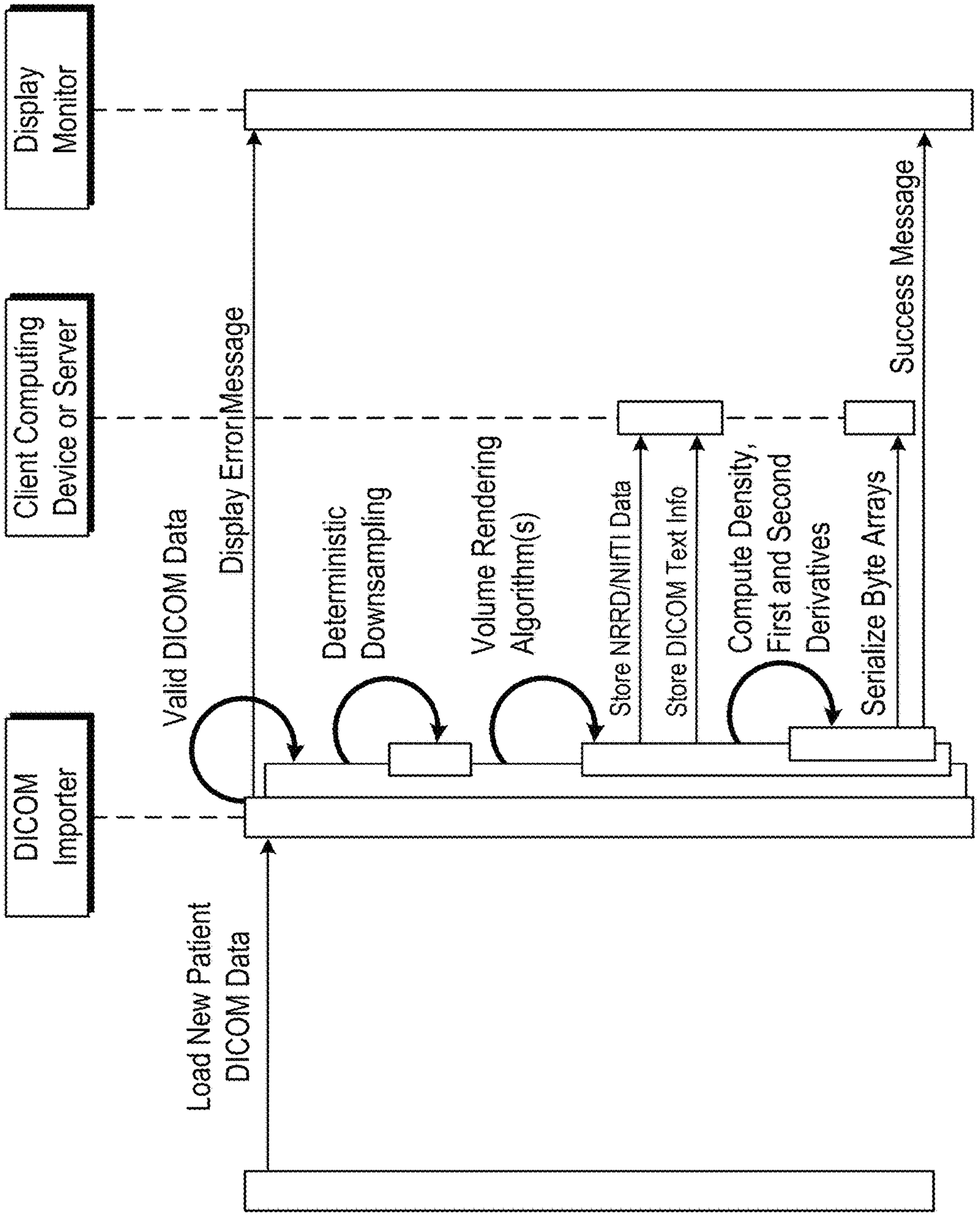
FIG. 3 is an exemplary sequence diagram illustrating the processing of image data for display by an XR display device, in accordance with at least one embodiment.

FIG. 3 is an exemplary sequence diagram illustrating the processing of DICOM data for display by an XR display device, in accordance with an embodiment of the present disclosure. First, a user (e.g., a clinician or clinical assistant) utilizes a client computing device to load a patient's DICOM data, for example, from an associated server (e.g., server 140), data store (e.g., data store 130), or from another device. The process first validates the DICOM data and may display an error message for invalid selected DICOM data. Upon successful validation of compliant DICOM data, the process then determines whether downsampling is needed for AR devices. In at least one embodiment, downsampling takes each DICOM image and applies the mean on each block from a computed integer factor parameter. For embodiments for which VR devices are used, downsampling may not be utilized. In at least one embodiment, the process generates two byte array, NRRD, or NITI datasets: one for VR devices that is not downsampled, and one for AR devices that is downsampled. The byte arrays, whether downsampled or not downsampled, still correspond to raw DICOM data.

A marching cubes algorithm can then be utilized to convert the raw patient DICOM byte array data into one or more 3D volumes representative of one or more isosurfaces. An exemplary marching cubes algorithm is now described. First, the algorithm starts with the volumetric dataset described by the DICOM data. The algorithm then iterates through each grid cell in the volumetric dataset and creates edge vertices through linear interpolation. A grid cell typically includes eight edge data points (vertices) forming a cube, and each cube edge vertex has a scalar value associated with it. For each grid cell, the scalar values at the vertices are evaluated to determine the location of the isosurface within the cube. The isosurface is a contour at a specific normalized value that separates regions of the dataset with different normalized values. The algorithm next uses a lookup table to determine the configuration of the isosurface within the cube based on the scalar values at the vertices. The lookup table provides a set of rules that map the scalar values to a specific set of triangles that represent the isosurface. Based on the configuration determined by the lookup table, the algorithm generates a set of triangles that represent the isosurface within the cube. These triangles are then combined with triangles from neighboring cubes to form a complete 3D mesh representation of one or more volumes. Further mesh refinement steps may be undertaken, such as smoothing, simplification, or surface reconstruction techniques, to improve the visual quality or performance of the resulting 3D mesh.

The data resulting from the marching cubes algorithm is then applied to a first and second derivative boundary analysis equation. The resulting values are then serialized into byte arrays and stored on a client computing device or directly on an XR display device. Information relating to the patient that is present in the DICOM data, such as patient name, series name, sex, study date, birthdate, etc., are stored in a JSON file. Upon process completion of the data processing, a success message may be generated.

Figure 4:
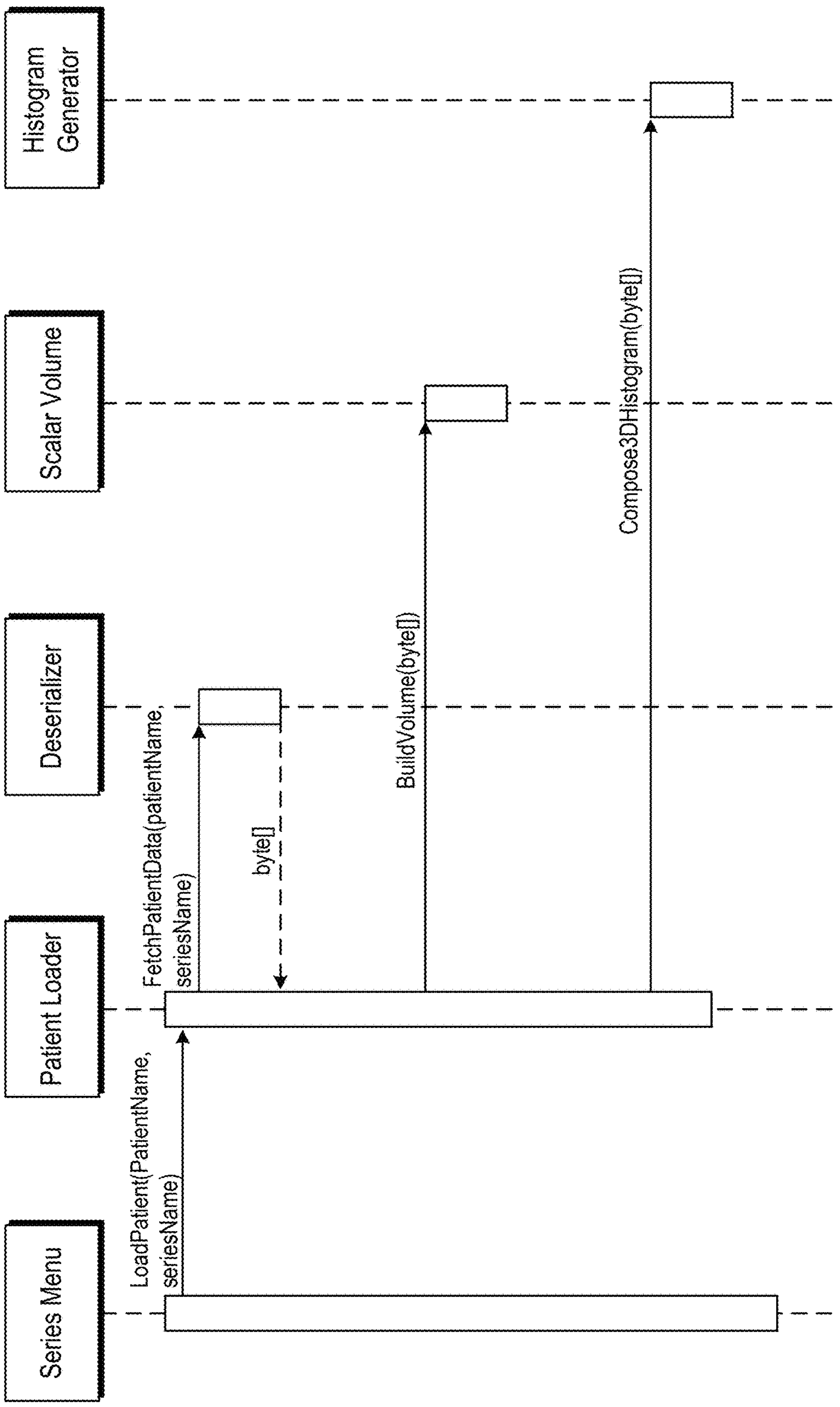
FIG. 4 is an exemplary sequence diagram illustrating how scalar volume data and 3D histogram data is generated, in accordance with at least one embodiment.

FIG. 4 is an exemplary sequence diagram illustrating how scalar volume data and 3D histogram data is generated, in accordance with an embodiment of the present disclosure. After a patient selects a particular scan from a patient Series Menu, the selected scan data (e.g., NRRD data) is sent to the Patient Loader component which calls the Deserializer component for deserializing the byte array from file into memory. The byte array is used to by a Scalar Volume and a Histogram Generator components to generate scalar volume data and 3D histogram, respectively, from the scan data. In at least one embodiment, the 3D histogram displays the values of the second derivative across all axes. The width can be computed by the range of data values produced from the marching cube algorithm, or a minimum width of 256 pixels in certain embodiments. The height can be computed based on the number of DICOM slices present in the patient series dataset, or a minimum of 128 pixels in some embodiments. Due to potential AR memory limitations, the depth may be limited to 8 pixels so the same histogram can be used interchangeably in both VR and AR display devices.

Figure 5:
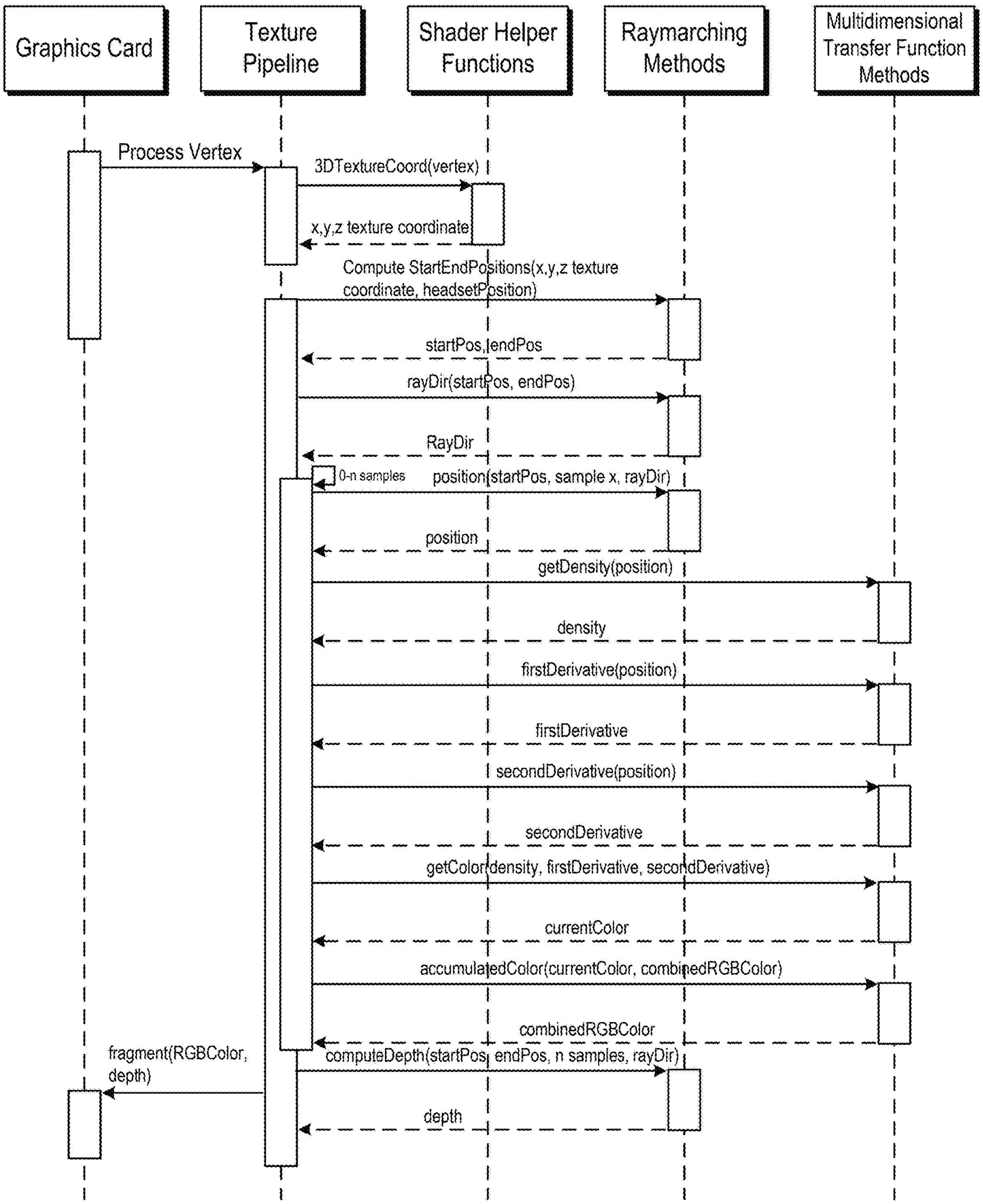
FIG. 5 is an exemplary sequence diagram illustrating an algorithm for applying a multidimensional transfer function to 3D density data, in accordance with at least one embodiment.

FIG. 5 is an exemplary sequence diagram illustrating an algorithm for applying a multidimensional transfer function to 3D density data via one or more multidimensional transfer function methods, in accordance with an embodiment of the present disclosure. An exemplary transfer function may compute the scalar data value, f(x), according to:

$$f(x) = v_{min} + (v_{max} - v_{min}) * \left(1 + \operatorname{erf}\left(x/\sigma\sqrt{2}\right)/2\right),$$

where $v_{max}$ and $v_{min}$ are high and low data value limits of the scanned object. The first derivative is computed according to:

$$f'(x) = \left(v_{max} - v_{min}/\sigma\sqrt{2}\right) * \exp\left(-\left(x^2/2\ \sigma^2\right)\right),$$

and second derivative is computed according to:

$$f''(x) = -\left(x(v_{max} - v_{min}))/\sigma^3\sqrt{2}\right) * \exp\left(-\left(x^2/2\ \sigma^2\right)\right).$$

Other transfer functions may also be used, which would be in the purview of those of ordinary skill in the art. In at least one embodiment, each vertex from the scalar volume is processed (e.g., by a graphics card of an XR display device or a client computing device communicatively coupled thereto) through a texture pipeline and returns a fragment for generating a voxel of display data. At the start of the pipeline, the vertex location is transferred to the scalar volume's coordinate (3D texture coordinate). In at least one embodiment, the scalar volume, and headset position coordinates determine the start and end positions, which can be used to compute the ray direction. Using the start and end position, n samples (e.g., up to 500 samples) are iterated along the ray direction from the start position to the end position using one or more raymarching methods. For each sample, the density, first derivative, and second derivative values are fetched from three-dimensional textures at the specified x,y,z coordinates. For each sample, the current color is fetched from the 3D histogram volume, and is accumulated with the previous sample values. After iterating through all samples, the depth is computed. The depth and color are then composed into a fragment for the graphics card. In at least one embodiment, this cycle repeats for every vertex in the marching cubes generated volume.

Figure 6:
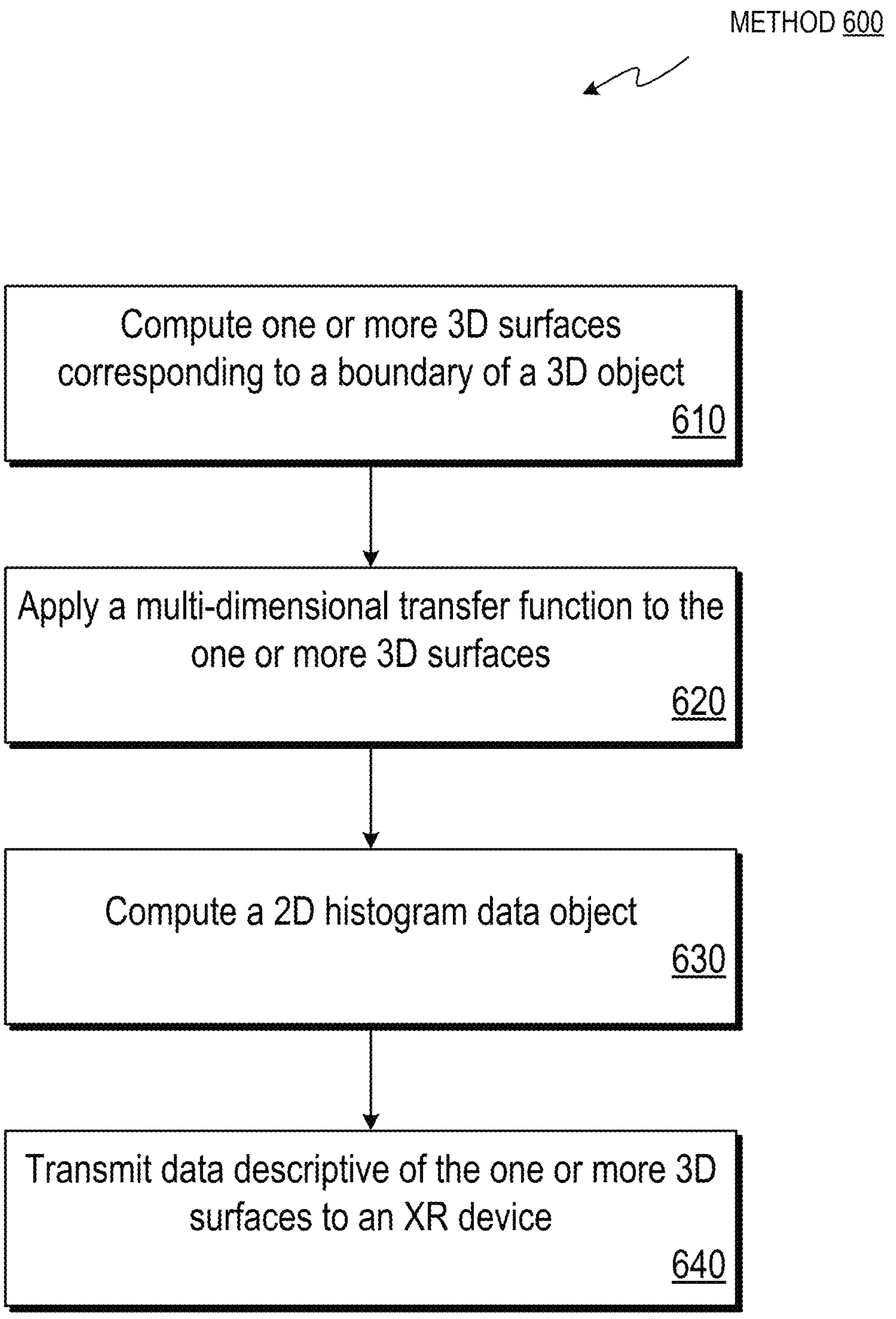
FIG. 6 is a flow diagram illustrating an exemplary method of reconstructing and displaying a 3D representation of an object from scalar volume data corresponding to a scan of the object with a medical imaging system, in accordance with at least one embodiment.

FIG. 6 is a flow diagram illustrating an exemplary method 600 of reconstructing and displaying a 3D representation of an object from scalar volume data corresponding to a scan of the object with a medical imaging system, in accordance with at least one embodiment. The method 600 may be performed by processing logic that includes hardware (e.g., circuitry, dedicated logic, programmable logic, microcode, etc.), software (e.g., instructions run on a processing device to perform hardware simulation), or a combination thereof. In some embodiments, the method 600 is performed by a processing device of the client computing device 110 or the server 140 described with respect to FIG. 1. In other embodiments, some of the functionality of the method 600 is distributed between the client computing device 110, the server, and/or the XR display device 160.

The method 600 begins at block 610, where the processing device computes one or more 3D surfaces corresponding to a boundary of the 3D object.

In at least one embodiment, computing the one or more 3D surfaces comprises applying an algorithm or method selected from marching cubes volume, direct volume rendering, volume ray casting, raymarching, ray tracing, shear warp, volume segmentation, early ray termination, empty space skipping, texture-based volume rendering, resampling, texture slicing, supersampling, parallel volume rendering, splatting, alpha blending, octree and BSP (binary space partitioning) space subdivision, multiple and adaptive resolution representation, isosurface rendering, maximum intensity projection, translucent, X-ray, domain volume rendering, full volume rendering, volumetric function interpolation, digital differential analyzer, non-photorealistic volume rendering, pre-integrated volume rendering, multi-pass occlusion culling, volumetric global illumination, spectral volume rendering, temporal reuse of voxels, high definition volume rendering, image-based meshing, Insight Toolkit (ITK) volume generation, noise, interpolation, linear filtering, cardinal spline function, central differencing, object-order, image-order, hybrid, anti-aliasing, aliasing, blurring, gradient filtering, pre-classified rendering, post-classified rendering, Taylor series expansion, front-to-back compositing, back-to-front compositing, gaussian filtering, post-classified model, Riemann sum, proximity clouds, image-level intermixing, accumulation level intermixing, illumination model level intermixing, time-critical rendering, issue, low-albedo optical model, dividing cubes, trimmed voxel lists, a marching tetrahedrons algorithm, or a combination thereof.

In at least one embodiment, the processing device down-samples the scalar volume data prior to computing the one or more 3D surfaces.

In at least one embodiment, the processing device utilizes DICOM rescale slope and rescale intercept to apply a linear transformation to form Hounsfield units, optical density, or other units. For example, the equation to calculate each voxel is:

HounsfieldUnit=voxelValue*rescale_slope+rescale_intercept.

In at least one embodiment, the processing device utilizes DICOM window center and window width for displaying voxels. The lowest visible voxel value can be calculated using the formula:

lowest Value=windowCenter−windowWidth/2.

The high visible voxel value can be calculated using the formula:

highest Value=windowCenter+windowWidth/2.

At block 620, the processing device applies a multi-dimensional transfer function to the one or more 3D surfaces. In at least one embodiment, applying the multi-dimensional transfer function comprises computing a first derivative and a second derivative of the scalar volume data along corresponding 3D spatial axes.

In at least one embodiment, applying the multi-dimensional transfer function comprises computing a first derivative and/or a second derivative of the scalar volume data along corresponding 3D spatial axes. For example, the processing device further computes a 2D histogram data object comprising axes corresponding to scalar volume data representative of the scanned object and the first derivative, and histogram bins representing a combination of the scalar volume data and the first derivative. In at least one embodiment, the 3D surface is computed based at least in part on the 2D histogram data.

At block 630, the processing device computes a 2D histogram data object comprising axes corresponding to the scalar volume data, the first derivative, and the second derivative, and histogram bins representing a combination of the scalar volume data, the first derivative, and the second derivative. In at least one embodiment, the 3D surface is computed based at least in part on the 2D histogram data.

In at least one embodiment, the processing device further, or alternatively, computes a 3D histogram volume data object comprising axes corresponding to the scalar volume data, the first derivative, and the second derivative, and histogram bins representing a combination of the scalar volume data, the first derivative, and the second derivative. In at least one embodiment, the 3D surface is computed based at least in part on the 3D histogram volume data.

At block 640, the processing device transmits data descriptive of the one or more 3D surfaces to an XR device (e.g., XR display device 160) to display the 3D representation of the object. In at least one embodiment, the XR device comprises an AR device or a VR device. In at least one embodiment, the method further comprises transmitting data descriptive of the one or more 3D surfaces to a plurality of XR devices simultaneously or near-simultaneously. In at least one embodiment, the plurality of XR devices are configured to view the 3D representation of the object within the same XR environment.

In at least one embodiment, the histogram is presented for display by the XR device as one or more adjustable 3D polygons for adjusting the volume data, first derivative, and the second derivative along an axis or axes. In at least one embodiment, the one or more adjustable 3D polygons comprises an adjustable 3D rectangular prism that allows for slicing inside or outside the displayed 3D volume, wherein the 3D volume is displayed within the 3D rectangular prism or the data is excluded from the 3D rectangular prism.

In at least one embodiment, a configurable endo-panel is presented for display by the XR device, the endo-panel comprising an available tool set follows a user while walking inside the 3D volume.

In at least one embodiment, the method further comprises transmitting the data descriptive of the one or more 3D surfaces comprises serializing the data into byte arrays. In at least one embodiment, the data descriptive of the one or more 3D surfaces is transmitted to the XR device as a 3D texture data object.

In at least one embodiment, the XR device is configured to display multiplanar reconstructions of the one or more 3D surfaces, which may be used to produce cross-sectional, panoramic, temporomandibular joint (TMJ), and bilaterial TMJ volumes or images.

In at least one embodiment, the scalar volume data is derived, extracted, or otherwise obtained from data stored in a DICOM data object generated by the medical imaging system during the scan of the object. In at least one embodiment, the scalar volume data corresponds to data obtained from one or multiple modalities selected from an arthogram scan, a computer tomography scan, an echocardiograph scan, an elastograph scan, a near-infrared spectroscopy scan, a magnetic particle imaging scan, a magnetic resonance imaging scan, a mammography scan, a myelogram scan, a photoacoustic imaging scan, a digital histopathology scan, a positron emission tomography scan, a projectional radiography scan, a tomosynthesis scan, an ultrasound scan, an x-ray scan, or any other medical scanner that produces DICOM images.

In at least one embodiment, the processing device further applies one or more machine learning algorithms to the one or more 3D surfaces for image classification and object detection.

Figure 7:
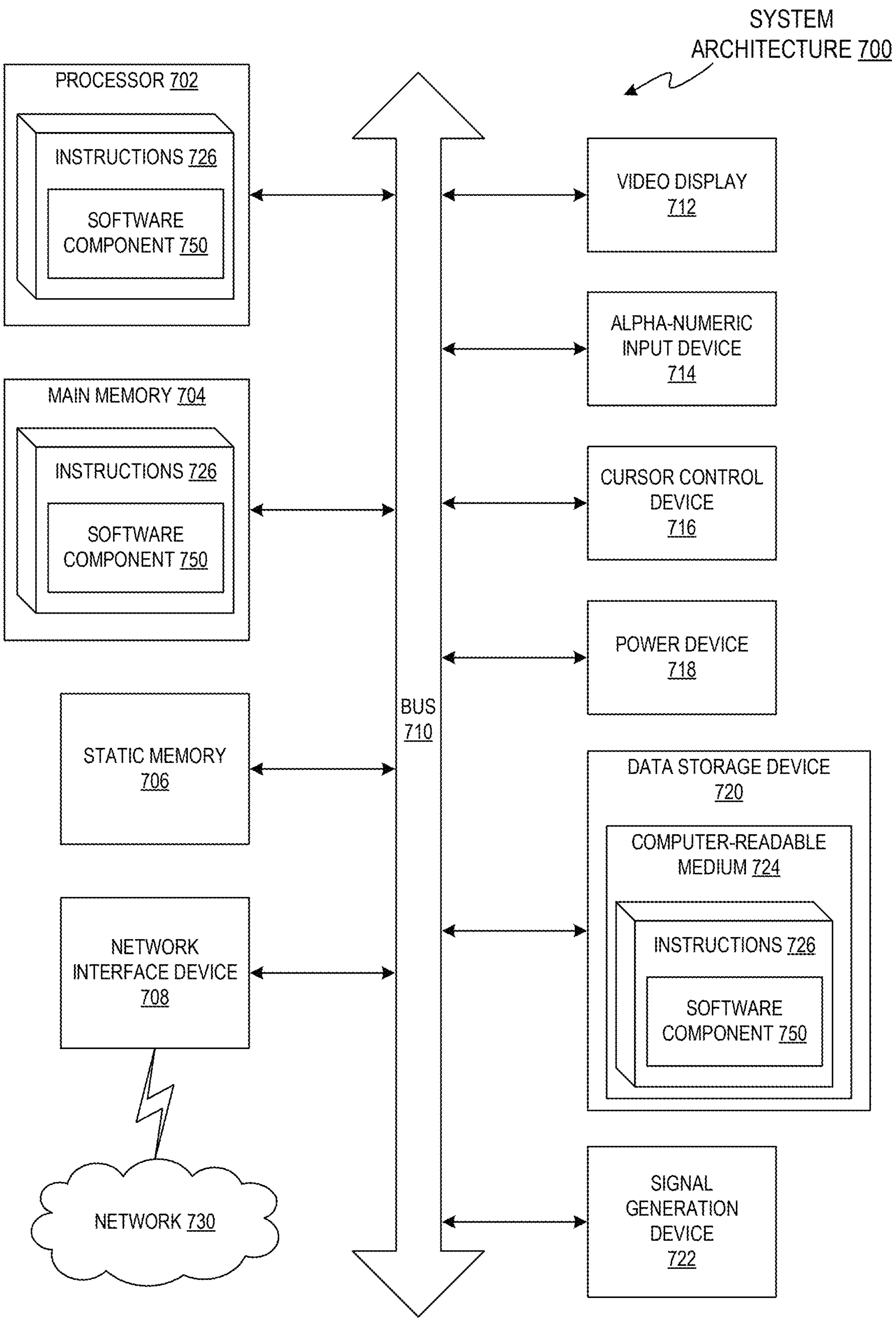
FIG. 7 is a block diagram illustrating an exemplary computer system, in accordance with at least one embodiment.

FIG. 7 illustrates a diagrammatic representation of a machine in the exemplary form of a computer system 700 within which a set of instructions (e.g., for causing the machine to perform any one or more of the methodologies discussed herein) may be executed. In alternative embodiments, the machine may be connected (e.g., networked) to other machines in a LAN, an intranet, an extranet, or the Internet. The machine may operate in the capacity of a server or a client machine in client-server network environment, or as a peer machine in a peer-to-peer (or distributed) network environment. The machine may be a personal computer (PC), a tablet PC, a set-top box (STB), a personal digital assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Some or all of the components of the computer system 700 may be utilized by or illustrative of any of the devices of the system architecture 100.

The exemplary computer system 700 includes a processing device (processor) 702, a main memory 704 (e.g., read-only memory (ROM), flash memory, dynamic random access memory (DRAM) such as synchronous DRAM (SDRAM) or Rambus DRAM (RDRAM), etc.), a static memory 706 (e.g., flash memory, static random access memory (SRAM), etc.), and a data storage device 720, which communicate with each other via a bus 710.

In some embodiments, the exemplary computer system 700 may further include a graphics processing unit (GPU) that comprises a specialized electronic circuit for accelerating the creation and analysis of images in a frame buffer for output to a display device. In some embodiments, because of its special design, a GPU may be faster for processing video and images than a CPU of the exemplary computer system 700.

Processor 702 represents one or more general-purpose processing devices such as a microprocessor, central processing unit, or the like. More particularly, the processor 702 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor 702 may also be one or more special-purpose processing devices such as an application specific integrated circuit (ASIC), a field programmable gate array (FPGA), a digital signal processor (DSP), network processor, or the like. The processor 702 is configured to execute instructions 726 for performing any of the methodologies and functions discussed herein, represented as software component 750.

The computer system 700 may further include a network interface device 708. The computer system 700 also may include a video display unit 712 (e.g., a liquid crystal display (LCD), a light-emitting diode (LED) display, a cathode ray tube (CRT), etc.), an alphanumeric input device 714 (e.g., a keyboard), a cursor control device 716 (e.g., a mouse), and a signal generation device 722 (e.g., a speaker).

Power device 718 may monitor a power level of a battery used to power the computer system 700 or one or more of its components. The power device 718 may provide one or more interfaces to provide an indication of a power level, a time window remaining prior to shutdown of computer system 700 or one or more of its components, a power consumption rate, an indicator of whether computer system is utilizing an external power source or battery power, and other power related information. In some embodiments, indications related to the power device 718 may be accessible remotely (e.g., accessible to a remote back-up management module via a network connection). In some embodiments, a battery utilized by the power device 718 may be an uninterruptable power supply (UPS) local to or remote from computer system 700. In such embodiments, the power device 718 may provide information about a power level of the UPS.

The data storage device 720 may include a computer-readable storage medium 724 on which is stored one or more sets of instructions 726 (e.g., software) embodying any one or more of the methodologies or functions described herein. The instructions 726 may also reside, completely or at least partially, within the main memory 704 and/or within the processor 702 during execution thereof by the computer system 700, the main memory 704 and the processor 702 also constituting computer-readable storage media. The instructions 726 may further be transmitted or received over a network 730 (e.g., the network 120) via the network interface device 708.

In some embodiments, the instructions 726 include instructions for one or more software components for implementing one or more of the methodologies or functions described herein. While the computer-readable storage medium 724 is shown in an exemplary embodiment to be a single medium, the terms "computer-readable storage medium" or "machine-readable storage medium" should be taken to include a single medium or multiple media (e.g., a centralized or distributed database, and/or associated caches and servers) that store the one or more sets of instructions. The terms "computer-readable storage medium" or "machine-readable storage medium" shall also be taken to include any transitory or non-transitory medium that is capable of storing, encoding, or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

For simplicity of explanation, the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events. Additionally, it should be appreciated that the methods disclosed in this specification are capable of being stored on an article of manufacture to facilitate transporting and transferring such methods to computing devices. The term "article of manufacture," as used herein, is intended to encompass a computer program accessible from any computer-readable device or storage media.

In the foregoing description, numerous details are set forth. It will be apparent, however, to one of ordinary skill in the art having the benefit of this disclosure, that the present disclosure may be practiced without these specific details. In some instances, well-known structures and devices are shown in block diagram form, rather than in detail, in order to avoid obscuring the present disclosure.

Some portions of the detailed description may have been presented in terms of algorithms and symbolic representations of operations on data bits within a computer memory. These algorithmic descriptions and representations are the mode through which those skilled in the data processing arts most effectively convey the substance of their work to others skilled in the art. An algorithm is herein, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the preceding discussion, it is appreciated that throughout the description, discussions utilizing terms such as "causing," "receiving," "retrieving," "transmitting," "computing," "modulating," "generating," "adding," "subtracting," "multiplying," "dividing," "deriving," "optimizing," "calibrating," "detecting," "performing," "analyzing," "determining," "enabling," "identifying," "modifying," "transforming," "applying," "comparing," "aggregating," "extracting," "downsampling," "upsampling," or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

The disclosure also relates to an apparatus, device, or system for performing the operations herein. This apparatus, device, or system may be specially constructed for the required purposes, or it may include a general purpose computer selectively activated or reconfigured by a computer program stored in the computer. Such a computer program may be stored in a computer- or machine-readable storage medium, such as, but not limited to, any type of disk including optical disks, compact disk read-only memories (CD-ROMs), and magnetic-optical disks, read-only memories (ROMs), random access memories (RAMs), erasable programmable read-only memories (EPROMs), electrically erasable programmable read-only memories (EEPROMs), magnetic or optical cards, solid-state drives (SSDs), or any type of media suitable for storing electronic instructions.

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application should generally be construed to mean "one or more" unless specified otherwise or clear from context to be directed to a singular form. Reference throughout this specification to "an embodiment," "one embodiment," or "some embodiments" means that a particular feature, structure, or characteristic described in connection with the embodiment is included in at least one embodiment. Thus, the appearances of the phrase "an embodiment," "one embodiment," or "some embodiments" in various places throughout this specification are not necessarily all referring to the same embodiment. Moreover, it is noted that the "A-Z" notation used in reference to certain elements of the drawings is not intended to be limiting to a particular number of elements. Thus, "A-Z" is to be construed as having one or more of the element present in a particular embodiment.

The present disclosure is not to be limited in scope by the specific embodiments described herein. Indeed, other various embodiments of and modifications to the present disclosure, in addition to those described herein, will be apparent to those of ordinary skill in the art from the preceding description and accompanying drawings. Thus, such other embodiments and modifications are intended to fall within the scope of the present disclosure. Further, although the present disclosure has been described herein in the context of particular embodiments in particular environments for particular purposes, those of ordinary skill in the art will recognize that its usefulness is not limited thereto and that the present disclosure may be beneficially implemented in any number of environments for any number of purposes.

What is claimed is:

1. A method executed by a processing device for reconstructing and displaying a three-dimensional (3D) representation of an object from scalar volume data corresponding to a scan of the object with a medical imaging system, the method comprising:

computing a 3D histogram volume data object comprising axes corresponding to the scalar volume data, a first derivative, and a second derivative, and histogram bins representing a combination of the scalar volume data, the first derivative, and the second derivative;

computing one or more 3D surfaces corresponding to a boundary of the 3D object based at least in part on the 3D histogram volume data;

applying a multi-dimensional transfer function to the computed one or more 3D surfaces; and transmitting data descriptive of the computed one or more 3D surfaces to an extended reality (XR) device to display the 3D representation of the object.

2. The method of claim 1, wherein applying the multi-dimensional transfer function comprises computing a first derivative and a second derivative of the scalar volume data along corresponding 3D spatial axes.

3. The method of claim 1, wherein applying the multi-dimensional transfer function comprises computing a first derivative of the scalar volume data along corresponding 3D spatial axes, and wherein the method further comprises:

computing a 2D histogram data object comprising axes corresponding to scalar volume data representative of the scanned object and the first derivative, and histogram bins representing a combination of the scalar volume data and the first derivative, wherein the 3D surface is computed based at least in part on the 2D histogram data.

4. The method of claim 3, further comprising: computing a 2D histogram data object comprising axes corresponding to the scalar volume data, the first derivative, and the second derivative, and histogram bins representing a combination of the scalar volume data, the first derivative, and the second derivative, wherein the 3D surface is computed based at least in part on the 2D histogram data.

5. The method of claim 1, wherein the histogram is presented for display by the XR device as one or more adjustable 3D polygons for adjusting the volume data, first derivative, and the second derivative along an axis or axes.

6. The method of claim 5, wherein the one or more adjustable 3D polygons comprises an adjustable 3D rectangular prism that allows for slicing inside or outside the displayed 3D volume, wherein the 3D volume is displayed within the 3D rectangular prism or the data is excluded from the 3D rectangular prism.

7. The method of claim 5, wherein a configurable endo-panel is presented for display by the XR device.

8. The method of claim 1, further comprising: prior to computing the one or more 3D surfaces, down sampling the scalar volume data.

9. The method of claim 1, wherein computing the one or more 3D surfaces comprises applying an algorithm or method selected from marching cubes volume, direct volume rendering, volume ray casting, raymarching, ray tracing, shear warp, volume segmentation, early ray termination, empty space skipping, texture-based volume rendering, resampling, texture slicing, supersampling, parallel volume rendering, splatting, alpha blending, octree and BSP (binary space partitioning) space subdivision, multiple and adaptive resolution representation, isosurface rendering, maximum intensity projection, translucent, X-ray, domain volume rendering, full volume rendering, volumetric function interpolation, digital differential analyzer, non-photorealistic volume rendering, preintegrated volume rendering, multi-pass occlusion culling, volumetric global illumination, spectral volume rendering, temporal reuse of voxels, high definition volume rendering, image-based meshing, Insight Toolkit (ITK) volume generation, noise, interpolation, linear filtering, cardinal spline function, central differencing, object-order, image-order, hybrid, anti-aliasing, aliasing, blurring, gradient filtering, pre-classified rendering, post-classified rendering, Taylor series expansion, front-to-back compositing, back-to-front compositing, gaussian filtering, post-classified model, Riemann sum, proximity clouds, image-level intermixing, accumulation level intermixing, illumination model level intermixing, time-critical rendering, issue, low-albedo optical model, dividing cubes, trimmed voxel lists, a marching tetrahedrons algorithm, or a combination thereof.

10. The method of claim 1, wherein transmitting the data descriptive of the one or more 3D surfaces comprises serializing the data into byte arrays.

11. The method of claim 1, wherein the data descriptive of the one or more 3D surfaces is transmitted to the XR device as a 3D texture data object.

12. The method of claim 1, wherein the XR device is configured to display multiplanar reconstructions of the one or more 3D surfaces.

13. The method of claim 1, wherein scalar volume data is derived, extracted, or otherwise obtained from data stored in a data object generated by the medical imaging system during the scan of the object, wherein the data object is a Digital Imaging and Communications in Medicine (DICOM) format, a Neuroimaging Informatics Technology Initiative format, or a Nearly Raw Raster Data (NRRD) format, wherein the scalar volume data corresponds to data obtained from one or multiple modalities selected from an arthogram scan, a computer tomography scan, an echocardiograph scan, an elastograph scan, a near-infrared spectroscopy scan, a magnetic particle imaging scan, a magnetic resonance imaging scan, a mammography scan, a myelogram scan, a photoacoustic imaging scan, a digital histopathology scan, a positron emission tomography scan, a projectional radiography scan, a tomosynthesis scan, an ultrasound scan, an x-ray scan, or any other medical scanner that produces DICOM images.

14. The method of claim 1, wherein the XR device comprises an augmented reality (AR) device or a virtual reality (VR) device.

15. The method of claim 1, further comprising transmitting data descriptive of the one or more 3D surfaces to a plurality of XR devices simultaneously or near-simultaneously, wherein the plurality of XR devices are configured to view the 3D representation of the object within the same XR environment.

16. The method of claim 1, further comprising:
- applying one or more machine learning algorithms to the one or more 3D surfaces for image classification and object detection.

17. A system for providing three-dimensional visualization of an object, the system comprising:
- a client computing device and/or a server; and
- the extended reality (XR) device operatively coupled to the client computing device and/or the server, wherein the client computing device and/or the server are adapted to perform the method of claim 1.

18. A non-transitory computer-readable medium having instructions encoded thereon that, when executed by a processing device, cause the processing device to perform the method of claim 1.

19. A method of presenting for display a three-dimensional (3D) representation of an object by an extended reality (XR) device, the method comprising:
- receiving, by the XR device:
  - data descriptive of one or more 3D surfaces representative of the object, the data derived from multi-dimensional transfer function applied to scalar volume data corresponding to a scan of the object; and
  - 3D histogram volume data descriptive of axes corresponding to the scalar volume data representative of the scanned object; and
  - generating for display the one or more 3D surfaces representative of the scanned object based on the 3D histogram volume data.

* * * * *